(12) United States Patent
Turner et al.

(10) Patent No.: US 7,416,530 B2
(45) Date of Patent: Aug. 26, 2008

(54) MEDICAL DEVICES

(75) Inventors: Nicholas McMahon Turner, York (GB); Peter Alfred Payne, North Tawton (GB); G. Alban Davies, York (GB); Julie A. Davies, York (GB); Simon John Patrick O'Riordan, Leeds (GB)

(73) Assignee: L & P 100 Limited, Leeds, Yorkshire (GB)

( * ) Notice: Subject to any disclaimer, the term of this patent is extended or adjusted under 35 U.S.C. 154(b) by 597 days.

(21) Appl. No.: 10/718,057

(22) Filed: Nov. 20, 2003

(65) Prior Publication Data

US 2005/0102026 A1 May 12, 2005

(30) Foreign Application Priority Data

Nov. 4, 2003 (GB) ............................ 0325679.9

(51) Int. Cl.
*A61B 5/05* (2006.01)
*A61F 2/24* (2006.01)

(52) U.S. Cl. .................. 600/485; 600/486; 623/2.1; 623/2.2; 623/2.38

(58) Field of Classification Search .............. None
See application file for complete search history.

(56) References Cited

U.S. PATENT DOCUMENTS

| | | | | |
|---|---|---|---|---|
| 3,671,979 A | * | 6/1972 | Moulopoulos | 623/2.11 |
| 4,979,955 A | * | 12/1990 | Smith | 623/2.2 |
| 5,032,128 A | * | 7/1991 | Alonso | 623/2.41 |
| 5,156,621 A | * | 10/1992 | Navia et al. | 623/2.12 |
| 5,487,760 A | * | 1/1996 | Villafana | 623/2.2 |
| 5,855,550 A | * | 1/1999 | Lai et al. | 600/300 |
| 5,967,986 A | | 10/1999 | Cimochowski et al. | |
| 6,053,873 A | | 4/2000 | Govari et al. | |
| 6,277,078 B1 | | 8/2001 | Porat et al. | |
| 6,331,163 B1 | * | 12/2001 | Kaplan | 600/486 |
| 6,409,675 B1 | | 6/2002 | Turcott | |
| 6,638,231 B2 | | 10/2003 | Govari et al. | 600/486 |
| 6,638,303 B1 | * | 10/2003 | Campbell | 623/2.2 |

(Continued)

FOREIGN PATENT DOCUMENTS

EP 0758542 A1 2/1997

(Continued)

OTHER PUBLICATIONS

Eitz, et al; Acoustic Phenomena and Valve Dysfunction in Cardiac Prosthesis: Data Acquisition and Collection via the Internet; J. Heart Valve Dis.; Jul. 2003; pp. 414-419; vol. 12 No. 4; ICR Publishers 2003.

(Continued)

*Primary Examiner*—Robert L. Nasser
(74) *Attorney, Agent, or Firm*—Bracewell & Giuliani LLP

(57) ABSTRACT

There is disclosed a medical device adapted to be implanted in the heart of a patient and operable therein i) as a heart valve; or ii) to assist in the functioning of one of the patient's heart valves; or iii) to monitor the functioning of one of the patient's heart valves. The device includes one or more sensors for sensing a physiologically or clinically relevant parameter of a patient. A telemetric communication device telemetrically transmits data related to a parameter sensed by the sensor to a remote device.

12 Claims, 3 Drawing Sheets

U.S. PATENT DOCUMENTS

| | | | |
|---|---|---|---|
| 2001/0051766 A1* | 12/2001 | Gazdzinski | 600/309 |
| 2002/0072656 A1 | 6/2002 | Vantassel et al. | |
| 2002/0120200 A1 | 8/2002 | Brockway et al. | |
| 2002/0151816 A1 | 10/2002 | Rich et al. | |
| 2002/0183628 A1* | 12/2002 | Reich et al. | 600/486 |
| 2003/0032993 A1 | 2/2003 | Mickle et al. | |
| 2003/0120159 A1 | 6/2003 | Mohler | |
| 2003/0139677 A1 | 7/2003 | Fonseca et al. | |
| 2003/0163055 A1* | 8/2003 | McLaughlin et al. | 600/504 |
| 2003/0195497 A1 | 10/2003 | Schoon et al. | |
| 2004/0085427 A1 | 5/2004 | Lee | |

FOREIGN PATENT DOCUMENTS

| | | |
|---|---|---|
| WO | WO01/09640 A1 | 2/2001 |
| WO | WO02/076289 A2 | 10/2002 |
| WO | WO2004/073513 A2 | 9/2004 |

OTHER PUBLICATIONS

*Wireless Pressure Sensing of Aneurysms*, T. Ohki, D. Stern, M. Allen and J. Yadav from Endovascular Today, Apr. 2004, pp. 47, 48, 50 and 52.

*Microchip Implants May Save Lives One Day*, Eleni Berger, Jan. 23, 2002, source unknown.

*Initial Animal Studies of a Wireless, Batteryless, MEMS Implant for Cardiovascular Applications*, N. Najafi and A. Ludomirsky from Biomedical Microdevices 6:1, 61-65, 2004.

*Developing Innovative Implantable Medical Devices*, D. Hodgins from Medical Device Technology, May 2004.

*Implantable Telemetric Pressure Measurement*, T. Eggers and M. Wenzel from Medical Device Technology, May 2004.

*Development and Validation of Implantable Sensors for Monitoring Function of Prosthetic Heart Valves: in vitro Studies*, C. Lanning and R. Shandas from Medical and Biological Engineering & Computing 2003, vol. 41 pp. 416-424.

*Biomedical Engineers Team With Hospital Clinicians on Advanced Devices for Cardiovascular Treatment*, Jul. 2, 2001 (web page).

*New CU-Boulder Program Links Engineering and Heart Health*, Jun. 18, 2003 (web page).

*Development of a Chronically Implantable Sensor System for Monitoring Prosthetic Heart Valve Function in vivo*, entitled Cover Page, (undated web page).

*Bioengineering and Materials Science*, (undated web page).

*Engineering Micro/Nano Systems in Engineering*, (undated web page).

* cited by examiner

MEDICAL DEVICES

RELATED APPLICATIONS

This application claims the benefit of United Kingdom Patent Application No. 0325679.9, filed on Nov. 4, 2003, which hereby is incorporated by reference in its entirety.

1. Field of the Invention

This invention relates to medical devices and systems that incorporate said medical devices, in particular to heart valve devices.

2. Background of the Invention

Heart valves are well known medical devices which are intended to replicate the function of the valves of the human heart, i.e., to regulate the flow of blood into or out of the chambers of the heart. Known heart valves can be categorized into two main types, namely mechanical heart valves and tissue heart valves. With mechanical valves, the entire valve is constructed from non-living material, which may be a synthetic or man-made material. They may comprise a tilting disc or occluder or incorporate a bileaflet design. Many mechanical valves, both occluders or bileaflet, are made from pyrolytic carbon, The disc or leaflets may be housed in a ring of titanium or pyrolytic carbon. Mechanical valves usually have a sewing cuff to aid the surgeon's implantation of these devices. They are usually made of a surgical cloth, either Dacron™ or Teflon™. In contrast, tissue valves are fabricated at least in part, using tissue obtained from a suitable living source. This tissue is treated, particularly chemically, to prevent degeneration, to reduce antigenicity and to extend shelf life of the valves as well as to strengthen them. Typically the tissue element uses porcine (pig) aortic valves with part of the aortic artery wall. Thus, porcine valve leaflets are a part of the integral functioning valve. Some tissue valves are fabricated from pericardial pieces, fashioned by shaping the pericardial tissue into artificial leaflets. (The pericardium is part of the membrane surrounding the heart.)

The majority of tissue valves are made from porcine aortic valves. They may be used after trimming etc, by themselves (freesewn valves or roots) or may be sutured into a synthetic frame (stented tissue valves). Plastic mono or homopolymers are an example of such frames. These stented or framed bioprosthetic tissue valves frequently have a sewing cuff added to ease implantation, similar to mechanical valves. These cuffs may be made of surgical cloth, e.g., Dacron™ or Teflon™ and may incorporate a cloth filler, e.g. Dacron™. Some sewing cuffs on these valves are made from pericardium. The majority of stented valves have the frame additionally covered by surgical cloth, into which the porcine material is attached by sutures. Some freesewn porcine valves are covered with a layer of pericardium. It will now be apparent that, broadly speaking, tissue valves can be categorized into two sub-sections. More specifically, stented tissue valves utilize a stent support for the tissue valve wall whereas, in contrast, stentless tissue valves do not utilize supports of this type for the tissue valve wall, and require extra layers of sutures in order to provide a usable product. It is generally recognized that stentless (also known as free sewn or freestent) tissue valves provide better performance, but suffer from the disadvantages of being rather difficult to implant and difficult to size properly.

The use of heart valves is widespread, with more than 180,000 heart valve operations being performed every year in the western world alone. It is likely that the annual number of heart operations will increase still further in the future. However, there are a number of problems associated with known heart valve devices. Firstly, there is a need to monitor patients who have had heart valves filled. At present, this post operative monitoring process may be inconvenient, resource intensive, and expensive. In particular, monitoring is most efficaciously performed through echocardiography, which requires the provision of expensive ultrasound equipment. Necessarily, such resources are only maintained at relatively large institutions such as hospitals, and thus require patients to travel (possibly over long distances) to attend a check up, which is inconvenient. A related problem is that access to echocardiography monitoring is limited in fact, it is the case that implanted heart valve dysfunction associated with abnormal valve action caused by complications such as thrombosis formation or tissue ingrowth tends to develop over a period of several weeks. This period cart occur between the initial monitoring by echocardiography and further physical examinations. Additionally, it would be highly desirable to obtain feedback on the clinical performance of a heart valve over a period of time. However, there is currently no readily available method for performing an in vivo assessment of this type which is not invasive or minimally evasive, or indeed avoids patients and clinicians waiting for appointments for full assessment to be performed. It is also not easy and somewhat subjective to compare one study with another or to evaluate the gradual changes over a period of time. Eitz et al (T Eitz, D Fritzsche, O Grimmig, I Frerichs, A Frerichs, G Helllge, K Minarni and R Korfer, J. Heart Valve Dis, 12 (2003) 414) discloses an approach to the monitoring of heart valves in which patients are trained to use briefcase sized acoustic detection devices to investigate heart functions and to transmit the data thus acquired. It is a disadvantage that the approach is entirely reliant on training the patients to perform an analytical technique and on the ability of the patients to properly perform the technique. US 2002/0072656 A1 and U.S. Pat. No. 6,409,675 (the contents of which are herein incorporated by reference) disclose apparatus which are implanted into the vascular system of an individual and which arc capable of providing information relating to clinically important parameters. The apparatus disclosed does not relate to heart valves and in particular to either valve replacement, either mechanical or tissue, or indeed to assessing the results of surgical invasive or minimally invasive procedures to repair or treat indigenous valve disorders or problems.

SUMMARY OF THE INVENTION

The present invention addresses the abovenamed problems, and, in particular, provides a straightforward, efficacious and economic means of obtaining clinically and physiologically useful in vivo data relating to the condition of a heart valve implant or repair or other indigenous valve treatment, arid of the performance of the heart valve. The in vivo data can be easily obtained on a regular basis over an extended time frame, Further, data can be obtained without requiring the attention of skilled operatives so as to provide the attendant clinical staff with an assessment of any changes, either acute or chronic, with the valve(s) progress since time of implant or treatment.

For the avoidance of doubt, the term "patient" as used herein includes both humans and animals within its scope.

According to a first aspect of the invention there is provided a medical device adapted to be implanted in the heart of a patient and operable therein i) as a heart valve; or ii) to assist in the functioning of one of the patient's heart valves; or iii) to monitor the functioning of one of the patient's heart valves; the device comprising:

one or more sensors for sensing a physiologically or clinically relevant parameter; and telemetric communication means for telemetrically transmitting data related to a parameter sensed by the one or more sensors to a remote device.

In the case of option i), above, the medical device is a heart valve which may further comprise a valve for regulating the flow of blood through the device. Typically, the valve comprises a number of leaflets, although this is not a limiting feature of the invention.

In the case of option ii), above, the medical device may comprise a heart valve repair device. The heart valve repair device may comprise a heart valve support structure, such as an annular support structure, Such annular structures may be sewn onto the top portion of a patient's heart valve.

In the case of option iii), above, the medical device may comprise a structure suitable for placement in or on a patient's heart valve. The patient's heart valve may be a treated indigenous valve or a valve which, although untreated, might require monitoring to determine when or if future treatment or replacement is required, In preferred embodiments, the telemetric communication means is a passive device which is powered by energy transmitted by a remote device, in which instance the telemetric communication means may be a transponder, such as an RF tag device. Alternatively, the telemetric communication means may be powered by an energy source disposed on or in physical connection with the medical device, such as a battery. Alternatively still, it may be possible to utilize energy produced by the patient, in particular energy associated with the beating of the patient's heart, to power the telemetric communication means.

The telemetric communication means may be powered by an RF field.

The telemetric communication means may transmit data using an RF field.

The telemetric communication means may transmit data by other means and/or be powered by other means, such as microwave or other electromagnetic radiation, acoustic signals or other electromagnetic fields.

In further embodiments, the telemetric communication means, the means by which the telemetric communication means transmits data and the means by which the telemetric communication means is powered may utilize technology known in the field of mobile telephones (also known as cell telephones). In such embodiments, the telemetric communication means may transmit data using Bluetooth (RTM), WLAN, GSM, GPRS or UMTS technology.

The telemetric communications means comprises an integrated circuit. The telemetric communication may comprise a chip, preferably a microchip.

At least one sensor may sense blood pressure. In this way, highly relevant clinical pressure data, such as systolic and diastolic pressures, and pressure profiles as a function of time, can be obtained. Advantageously, the medical device comprises at least two spaced apart sensors for sensing blood pressure at different locations in the heart of the patient. In this instance the telemetric communication means may telemetrically transmit data related to the difference in the blood pressures sensed by the at least two sensors. In this way, information on blood flow and blood leakage can be obtained, particularly pressure differences across the valve or valve replacement, giving valuable data concerning valve narrowing/stenosis/incompetence.

At least one sensor may sense acoustic signals. In this way, highly relevant clinical data relating to heart beat can be obtained. In particular the performance of the valve(s) repair may be assessed, taking into consideration any abnormal rhythm and thus pressure profiles that might affect the interpretation of the telemetrically produced acoustic signal of the valve(s) performance. Additionally, information relating to blood flow, e.g., whether blood flow is normal or abnormal, can be obtained.

Advantageously, the one or more sensors sense blood pressure and acoustic signals. Blood pressure, pressure profiles and pressure differences may be sensed. A single sensor may sense blood pressure and acoustic signals.

One or more sensors may sense other physiologically relevant parameters, such as temperature and pH.

At least one sensor may be a passive sensor, i.e., a sensor that does not require a power source in order to operate as a sensor.

At least one sensor may be a piezoelcetric sensor. The piezoclectric sensor may comprise a polymeric active sensing area and the polymeric active sensing area may comprise polyvinylidene fluoride (PVDF) or a related PVDF material. PVDF is a preferred material since it is possible to provide PVDF sensors that can monitor both pressure and acoustic signals. Related PVDF materials include copolymers with PVDF, such as a PVDF-trifluorethylene (TrFe) copolymer.

The sensors and telemetric communication means may be disposed on the medical device so that, when implanted as a heart valve, these elements are situated either in an intravascular configuration or in an extravascular configuration. The sensors can be disposed so as to be in direct contract with blood once implanted. This provides higher signal values. However, it is generally preferred that the sensors are disposed so as to be out of direct contact with the blood, or on the external surface of a valve implant or within any material utilized for valve repair of an indigenous valve. Such a sensor or group of sensors may be outside the main blood flow stream.

The medical, device may be a tissue valve device having a valve wall formed from tissue. The medical device may be stented or stentless. In particular, the medical device may further comprise a stent support for the valve wall, in which at least one sensor and the telemetric communication means are disposed between the stent support and the valve wall.

A tissue valve medical device may further comprise a protective cover disposed around the periphery of the device, and the at least one sensor and the telemetric communication means may be disposed between the valve wall and the protective cover. The protective cover may comprise a polymeric layer, such as Dacron (RTM) or a pericardial layer, typically one that has been crosslinked.

The medical device may be a mechanical heart valve.

According to a second aspect of the invention there is provided a system for monitoring a patient comprising a medical device according to the first aspect of the invention and a remote device for receiving data telemetrically transmitted by a telemetric communication means.

It is highly advantageous that data obtained in vivo from the environs of a heart valve can be conveniently transmitted to a remote device with little or no inconvenience to the patient. Systems of the present invention can be produced economically, thus facilitating mass manufacture arid monitoring of the patient in a wide range of locations such as, for example, a general practitioner's surgery or at the patient's abode. It is a further advantage that the remote device can be a handheld device, thus further facilitating convenient usage. The system does not require the attention of a skilled operative in order to obtain data, and might even be used by the patient himself or herself.

The remote device may be adapted to provide power remotely to the telemetric communication means. The remote device may be adapted to produce an RF field for this purpose.

The remote device may comprise memory for storing data transmitted by the telemetric communication means. The remote device may comprise data analysis means for performing a physiologically or clinically relevant analysis of data transmitted by the telemetric communication means. An example of data analysis is provided by the instance in which two or more sensors sense blood pressure at different locations in the heart of the patient. In this instance, the remote device (or another component in the system) may calculate a quantity related to the difference in the blood pressures sensed by the two or more sensors. This quantity may be integrated with acoustic or other relevant clinical data, thus aiding enhanced clinical evaluation of the performance of the valve or valve replacement.

The remote device may comprise data transmission means. The data transmission means may comprise an interface suitable for sending data to the outside world, preferably to a computer. Data may be sent via a network, suitable but non-limiting examples of which are a wide area network (WAN), a local area network (LAN), an intranet, a worldwide computer network, and the Internet.

The system may further comprise a data storage device which is separate to the remote device, in which the remote device comprises means to write data on the data storage device. The data storage device may be a card having a magnetic data storage area, a digital versatile disc (DVD), a compact disc (CD) or another disc data storage medium. In this way, a record of in vivo data may be built up in a highly convenient manner. The assembled data record on the data storage device might be transported to a skilled physician for analysis and interpretation of the data in order to assess the patient, and/or might be used to assess the performance of the medical device itself, In either instance, the analysis, interpretation or assessment might be performed at a location which is remote from the location at which data were transmitted to the remote device.

According to a third aspect of the invention there is provided the use of a medical device according to the first aspect of the invention as a heart valve and in sensing a physiologically or clinically relevant parameter. According to a fourth aspect of the invention there is provided the use of a medical device according to the first aspect of the invention to assist in the functioning of one of a patient's heart valves and in sensing a physiologically or clinically relevant parameter. According to a fifth aspect of the invention there is provided the use of a medical device according to the first aspect of the invention in, on or in the immediate environs of the heart valve of a patient to sense a physiologically or clinical relevant parameter and thereby monitor the functioning of said heart valve.

BRIEF DESCRIPTION OF THE DRAWINGS

Embodiments of medical devices and systems in accordance with the invention will now be described with reference to the accompanying drawings, in which.

DETAILED DESCRIPTION OF THE INVENTION

Figure 1:
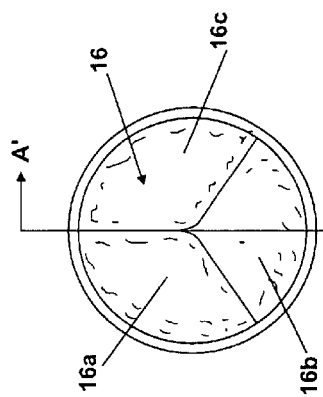
FIG. 1 is a side view of a stented heart valve in accordance with the invention.
Figure 2:
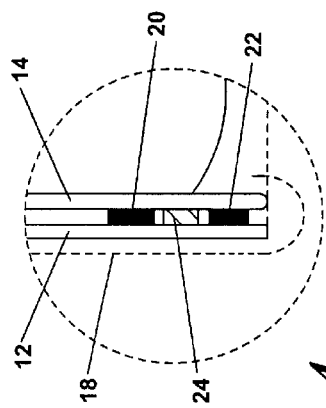
FIG. 2 is a plan view of the heart valve of FIG. 1.
Figure 3:
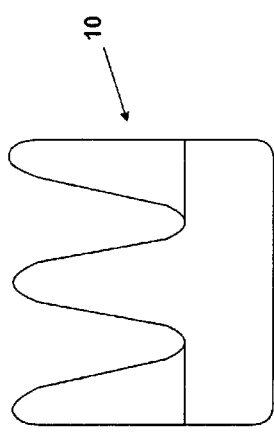
FIG. 3 is a cross sectional view of the heart valve of FIG. 1, taken along the line the line 3-3 of FIG. 2.
Figure 4:
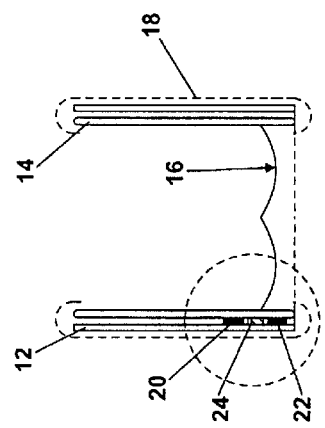
FIG. 4 is an enlarged view of a portion of the heart valve as shown in FIG. 3.
Figure 5:
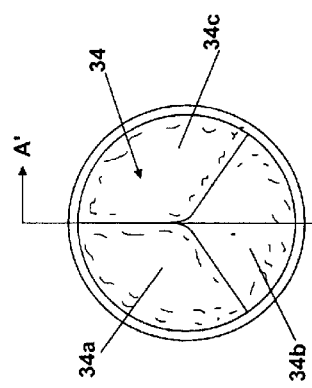
FIG. 5 is a side view of a freesewn heart valve in accordance with the invention.
Figure 6:
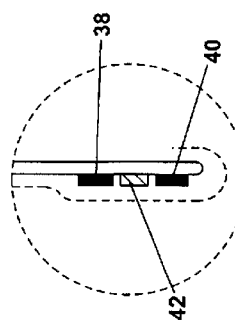
FIG. 6 is a plan view of the heart valve of FIG. 5.
Figure 7:
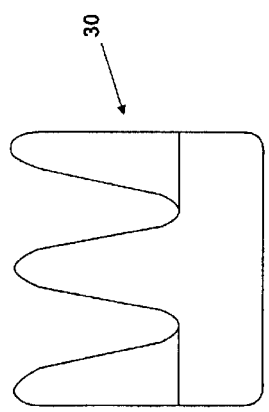
FIG. 7 is a cross sectional view of the heart valve of FIG. 5, taken along the line 7-7 of FIG. 6.
Figure 8:
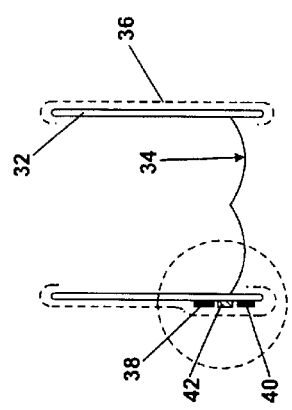
FIG. 8 is an enlarged view of a portion of the heart valve as shown in FIG. 7.

FIGS. 1-4 show a first embodiment of a heart valve 10 according to the invention. The heart valve 10 is a stented tissue valve comprising a stent 12 which supports a tissue valve wall 14 obtained from a suitable source. Typically, porcine tissue valves are utilized. The tissue valve 10 further comprises a valve 16, the valve 16 being made up of three tissue leaflets 16a, 16b, 16c. Typically, a protective cover 18 is provided around the periphery of the valve wall 14/stent 12. The cover may be produced from any suitable material: typically, a polymeric sheet material such as Dacron (RIM) is used, although the invention is not limited in this regard. As shown to best effect in FIG. 4, the tissue heart valve 10 further comprises a first sensor 20, a second sensor 22, and telemetric communication means 24, all of which are disposed in the cavity provided between the valve wall 14 and stent 12. This location is extremely convenient, since blood flowing through the tissue heart valve 10 is not in direct contact with the sensors 20, 22 or telemetric communication means 24, but the sensors are sufficiently close to the blood flow to be able to detect certain desired parameters associated with the blood flow with good sensitivity. As will be explained in more detail below, it is desirable that the sensors 20, 22 are disposed on either side of the valve 16.

FIGS. 4-8 depict a second embodiment of the present invention which is a free sewn (or stentless) tissue heart valve 30. The tissue heart valve 30 comprises a tissue valve wall 32 and a tissue valve 34, the tissue valve 34 itself comprising a plurality of leaflets 34a, 34b, 34c. Again, it is typical that porcine tissue is used to fabricate the tissue heart valve 30, although the invention is not limited in this regard. The tissue valve 30 further comprises a protective layer 36, which typically is a crosslinked pericardial cover also obtained from sources of porcine tissue. The tissue heart valve 30 further comprises a first sensor 38, a second sensor 40 and telemetric communication means 42 which are disposed between the valve wall 32 and the pericardial cover 36. In common with the first embodiment, it is advantageous that the first and second sensors 38, 40 are disposed on either side of the valve 34. Additionally, it is highly advantageous that the sensors 38, 40 and telemetric communication means 42 are situated in a location which is not in, direct contact with blood flowing through the heart valve, but which is close enough to enable the desired. parameters to be sensed with good sensitivity.

Manufacturing techniques and processes such as crosslinking of tissue and suturing of the heart valve structure may be employed in ways well known in the art. The skilled reader will readily appreciate that appropriate suturing can be employed in order to seal the sensors and telemetric communication means in place in between various layers as described above with reference to the first and second embodiments.

One or more sensors may be employed in a heart valve of the present invention in order to sense one or more physiologically or clinically relevant parameters. Examples of such parameters include pressure, acoustic signals, temperature and pH. Chemical sensors and biosensors might be used in order to analyze blood flowing through a heart valve, Pressure and acoustic signal measurements are particularly important. Measurement of pressure can provide systolic and diastolic pressure information. Furthermore, it is possible to obtain useful information by examining the differences in pressures measured by two or more pressure sensors. Particularly useful information is obtained when sensors are disposed either side of the valve, such as described above in relation to the first and second embodiments of the invention. In this way, blood flow can be assessed, and leakage across or from the valve can be detected, By sensing acoustic signals, it is possible to obtain information relating to patterns of heartbeat. For example, it is possible to detect abnormal events, such as heart murmurs.

It is advantageous to utilize piezoelectric sensors in devices of the present invention, although the invention is not limited in this regard. In preferred embodiments, at least one PVDF based transducer is utilized. An advantage associated with PVDF transducers is that they can be operated as both a pressure transducer and as a microphone, monitoring acoustic signals. In the pressure transducer mode, the PVDF transducer is reacting to blood pressure during the heart cycle. In the microphone mode, the PVDF transducer is listening to the sounds emitted by the blood as it moves through the heart valve. This requires that the PVDF transducer has a band width out to 1 or 2 kHz. Devices of this nature have been described in the literature, but not in the context of heart valves (see, for example, "Tactile Sensors for Robotics in Medicine", edited by John G Webster, John Wyley, 1988, particularly chapter 8, "Piezoetectric Sensors", and "The Applications of Ferroelectric Polymers", Chapman and Hall, 1988, in particular chapter 8, "Microphones, Headphones and Tone Generators", the contents of both of which are herein incorporated by reference). PVDF is inherently a very high impedance material, but in the context of acoustic signals, it is not necessary to use very thin materials. In non-limiting examples, a PVDF thickness of between 60 and 150 μm, preferably between 60 and 110 μm, is used. It is advantageous that it is possible to use relatively large area transducers. Other piezoelectric materials might be used in place of PVDF. In particular, there are numerous polymer based composite materials which could be used. Lead zirconate titantate (PVT) is an example of another suitable piezoeleciric material which is not polymeric in nature.

Figure 9:
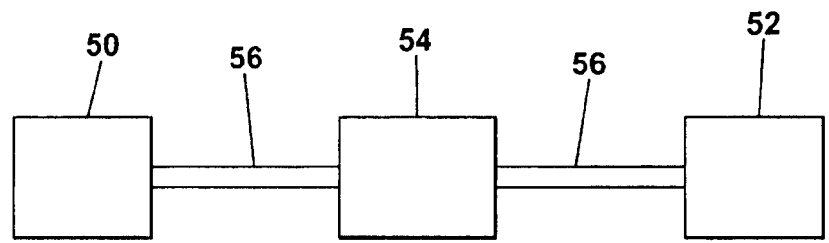
FIG. 9 shows an arrangement of two sensors and telemetric communication means.

FIG. 9 shows a sensing arrangement comprising two sensors 50, 52 in connection, with telemetric communication means 54 through wiring 56, such as gold wires. Other ways of connecting the sensors to the telemetric communication means would suggest themselves readily to the skilled reader. The function of the telemetric communication means 54 is to telemetrically transmit data related to a parameter sensed by one or more of the sensors 50, 52 to a remote device. It is understood that the medical devices provided by the present invention are intended to be able to transmit data obtained in vivo within a patient who has had the heart valve implanted therein, the data being transmitted out of the body of the patient. The heart valve might be implanted in any of the precise locations in the heart that known heart valves are implanted, using known surgical techniques.

It is anticipated that in practice the data will be directly transmitted from the telemetric communication means to a remote device disposed outside of the body of the patient. However, in principle at least, it may be possible to send data from the telemetric communication means to another device positioned in the body of the patient, e.g., subcutaneously. This device might transmit data (possibly after performing datalogging or data analysis functions) to a further device disposed outside of the body of the patient. In a preferred embodiment, the telemetric communication means 54 is a so-called RF tag device (such devices are also known as radio frequency identification (RFID) chips—see, for example, UK periodical "Computing", 16 Jan. 2003 edition). Such devices are well known for position monitoring purposes. For example, animals such as cattle and pets may be monitored in this way using a RF tag positioned subcutaneously. RF tag devices are passive devices until interrogated by a suitable, and typically relatively powerful, RF signal. The signal is energetic enough to power up the RF tag device which, in the context of position measurement, typically responds with some form of electronic bar code signal, typically using a response frequency around 450 MHZ. For the purposes of the present invention, the function of the RF tag is altered somewhat from these prior art applications.

In particular, the RF tag accepts data from the sensors, and transmits data relating to measurements made by the sensors to the interrogating remote device. One way in which this can be achieved is to use the signal from, the sensors to modulate the response from the RF tag in a suitable manner. The remote device accepts the data transmitted telemetrically by the RF tag device, and can perform desired functions such as datalogging, data analysis and data presentation. Additionally, the remote device transmits a RF signal to the telemetric communication means in, order to power said telemetric communication means. Alternatively, it may be possible to build some or all of the datalogging and data analysis functions into the functionality of the telemetric communication means.

Figure 10:
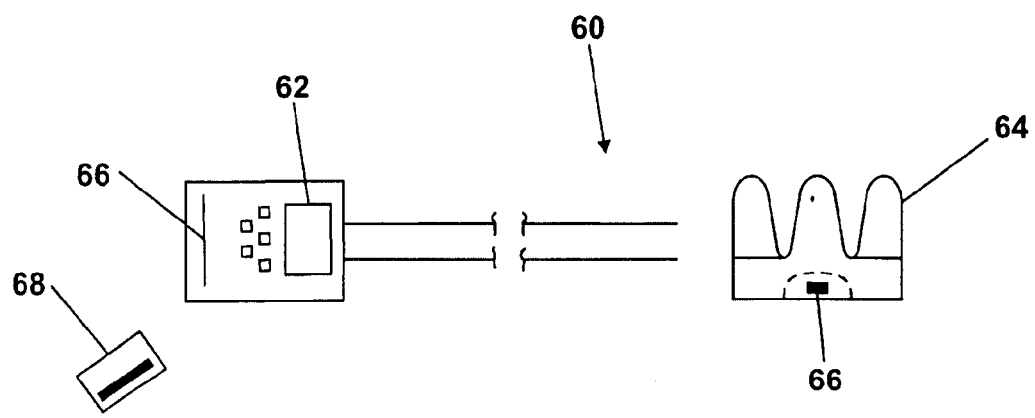
FIG. 10 shows a system in accordance with the invention.

It is often desirable that the data obtained using the present invention are communicated to a site which is different to the site at which the in vivo measurements were made. For example, for the convenience of the patient, it is desirable to make the in vivo measurements at accessible locations such as a general practitioner's surgery or the patient's abode. Equally, it is convenient for a physician or other skilled person who is intended to analyze the data that the data may be conveyed in some way to a location, which is convenient for that skilled person. The present invention is highly convenient in this regard, since the remote device can be configured to transmit data over a network such as a WAN, LAN, intranet, worldwide computer network, or the internet. Alternatively, or additionally, the remote device might write the data to a suitable data storage device such as a DVD, a CD or another form of disc storage medium. Very conveniently, the remote device might be configured to write data to a card having a suitable data storage area such as a magnetic data storage area. In this way, the patient can be provided with a "swipe card" on which relevant data can be written. The swipe card can then be conveyed to an interested party for data analysis. FIG. 10 depicts one embodiment of a system 60 of the invention comprising a remote device 62 and a heart valve 64. The heart valve 64 has telemetric communication means 66 for telemetrically transmitting data to the remote device 62. It is understood that the heart valve 64 is implanted in the heart of a patient (not shown). The remote device 62 has a slot 66 through which a swipe card 68 can be translated, thereby permitting data recorded by the heart valve 64 to be stored on the swipe card 68.

There are numerous variations possible which fall within the general ambit of the invention. The first and second embodiments discussed above utilize sensors and telemetric communication means which are, strictly speaking, anchored intravascularly, since these components are disposed inside of the vascular "tree". It is also possible to dispose these components in an extravascular configuration, or to position them in a strict intravascular sense, i.e., disposed in the blood flow. The sensors and telemetric communication means may be protected by a suitable shell, layer or membrane, or even encapsulated by same. A passive telemetric communication means might be powered by means other than the supply of RE energy. For examples the heart valve might be provided with coils which can be powered up using externally supplied electromagnetic fields other than RF fields. Alternatively still, it may be possible to provide "active" telemetric communication means, rather than a passive one, which is powered internally, allowing continuous or near continuous operation. The sensors may be powered in the same manner. In this case, data from the sensors might be accumulated continuously, rather than on demand when interrogated by the remote device. There are numerous possibilities regarding datalogging and data analysis functions. For example, it may be desirable to only store, process, or notify the existence of data which relate to adverse events. It is possible to provide mechanical heart valves which incorporate in vivo sensing capabilities of the type generally described above, Furthermore, it is possible to "retrofit" to existing heart valves, in order to provide modified existing heart valves so as to provide the in vivo sensing capabilities of the present invention. Another possibility still is to incorporate the sensors and telemetric communication means in a heart valve repair device. Heart valve repair devices are quite commonly used to repair mitral heart valves, although the invention is not limited in this regard. Typically, a support structure, such as a hoop is used, the support structure being sewn into the top of the valve. The hoop may comprise a plastic and may be provided with a cloth cover. It would be possible to dispose the sensor(s) and telemetric communication means within or on such a support structure.

The invention claimed is:

1. A medical device adapted to be implanted in the heart of a patient and operable therein i) as a heart valve; or ii) to assist in the functioning of one of the patient's heart valves; the medical device comprising;

at least one sensor for sensing a physiologically or clinically relevant parameter of the patient wherein said at least one sensor includes a piezoelectric sensor comprising a polymeric active sensing area which senses blood pressure of the patient;

telemetric communication means comprising an RFID device for telemetrically transmitting data related to the parameter sensed by the sensor to a remote device; and wherein said at least one sensor includes at least two spaced apart piezoelectric sensors for sensing blood pressure at different locations in the heart of the patient, each of the spaced apart sensors comprising a polymeric active sensing area which senses blood pressure of the patient.

2. The medical device according to claim, 1 wherein the medical device comprises a heart valve for regulating the flow of blood through the medical device.

3. The medical device according to claim 1 wherein the telemetric communication means comprises an integrated circuit.

4. The medical device according to claim 1 wherein said piezoelectric sensors also sense acoustic signals.

5. The medical device according to claim 4 wherein said piezoelectric sensors sense both blood pressure and acoustic signals.

6. A medical device according to claim 1 wherein the polymeric active sensing area comprises PVDF.

7. The medical device according to claim 1 wherein the medical device comprises a tissue valve device having a valve wall formed from tissue.

8. The medical device according to claim 7 further comprising a stent support for the valve wall, and wherein the piezoelectric sensors and the telemetric communication means are disposed between the stent support and the valve wall.

9. The medical device according to claim 7 wherein the medical device is stentless.

10. The medical device according to claim 7 further comprising a protective cover disposed around the periphery of the medical device, and wherein the piezoelectric sensors and the telemetric communication means are disposed between the valve wall and the protective cover.

11. The medical device according to claim 1 wherein the medical device comprises a mechanical heart valve.

12. A medical device adapted to be implanted in the heart of a patient and operable therein i) as a heart valve; or ii) to assist in the functioning of one of the patient's heart valves; the medical device comprising;

at least one sensor for sensing a physiologically or clinically relevant parameter of the patient wherein said at least one sensor includes a piezoelectric sensor comprising a polymeric active sensing area which senses blood pressure of the patient;

telemetric communication means comprising an RFID device for telemetrically transmitting data related to the parameter sensed by the sensor to a remote device;

wherein said at least one sensor includes at least two spaced apart piezoelectric sensors for sensing blood pressure at different locations in the heart of the patient, each of the spaced apart sensors comprising a polymeric active sensing area which senses blood pressure of the patient; and wherein the telemetric communication means telemetrically transmits data related to the difference in the blood pressures sensed by the at least two spaced apart sensors.

* * * * *